United States Patent
Grove (10) Patent No.: US 7,347,549 B2
(45) Date of Patent: Mar. 25, 2008

(54) RAPID SWITCHING SLIT SCAN IMAGE CAPTURE SYSTEM

(75) Inventor: Donald Charles Grove, Layton, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 483 days.

(21) Appl. No.: 10/732,704

(22) Filed: Dec. 10, 2003

(65) Prior Publication Data

US 2005/0134797 A1    Jun. 23, 2005

(51) Int. Cl.
*A61B 3/14* (2006.01)

(52) U.S. Cl. .................. 351/206; 351/314; 351/221

(58) Field of Classification Search ............... 351/205, 351/214, 221, 206
See application file for complete search history.

(56) References Cited

U.S. PATENT DOCUMENTS

| | | | | |
|---|---|---|---|---|
| 4,732,466 A | * | 3/1988 | Humphrey | 351/206 |
| 4,854,692 A | | 8/1989 | Kobayashi | 351/221 |
| 5,512,965 A | | 4/1996 | Snook | 351/205 |
| 5,512,966 A | | 4/1996 | Snook | 351/203 |
| 5,848,188 A | | 12/1998 | Shibata et al. | 382/203 |
| 6,575,573 B2 | * | 6/2003 | Lai et al. | 351/212 |
| 6,692,126 B1 | * | 2/2004 | Xie et al. | 351/212 |

FOREIGN PATENT DOCUMENTS

WO    WO 03/039332 A2    5/2003

\* cited by examiner

*Primary Examiner*—Huy Mai (57) ABSTRACT

A slit scan image capture system 14 or 15 for obtaining slit images of a patient's eye 28. At least two slit masks 16 and 18 or two moving mirrors 25 and 27 are associated with at least two rapid switching light sources 20 and 22 or 21 and 22 for illuminating slit images on a patient's eye 28. Two motors 24 and 26 or 29 and 31 each are connected to the slit masks 16 and 18 or movable mirrors 25 and 27 for incrementally moving the illuminated slits across the eye 28 to plurality of positions. A video camera 30 captures images of the illuminated slits on the eye 28 and a frame grabber 32 is connected to the video camera for storing the captured images. The rapid switching light sources 20 and 22 are powered-up to an approximately full power state and powered-down to an effectively off state in an amount of time less than an amount of time required by the motors 24 and 26 or 29 and 31 to move the slit masks 16 or 18 or movable mirrors 25 and 27 from one position to a next position. This minimizes the amount of time required to capture a plurality of slit images across major portions of the patient's eyes 28.

15 Claims, 9 Drawing Sheets

RAPID SWITCHING SLIT SCAN IMAGE CAPTURE SYSTEM

BACKGROUND OF THE INVENTION

1. Field of the Invention

The present invention relates to slit scan image capture systems for diagnostic evaluation of a patient's eyes. More specifically, the present invention is directed to slit scan image capture systems using rapid switching light sources, such as high luminescence light emitting diodes (HL-LEDs) or lasers.

2. Description of Related Art

In traditional slit scanning image capture systems, such as the Orbscan™, available from Bausch & Lomb Incorporated, the slit light source is focused white light from an incandescent source. These types of light sources typically have a relatively long period of time required to power-up to a full power state and to deactivate or power-down to a zero power state. This period of time is typically in the hundreds of milliseconds.

These long power-up and power-down time periods require the slit lamps to be fully powered-up during the duration of an eye exam on a patient. For example, the Orbscan™ is a moving slit system which requires the slit to be moved incrementally across the eye from time to time and at other times, the slit is to remain stationary for an image to be captured by the system.

As a motor causes a slit source to move, thereby causing a slit illumination to be moved across the eye, this movement causes a smear of light across the eye. This smear makes the image useless for analysis, and is therefore discarded. This discarded image reflects an amount of time that the patient is required to hold their eye still, but yet no data is acquired. This time period therefore represents an opportunity for increased efficiency in obtaining slit images.

Reducing the amount of exam time for obtaining eye images is important in order to reduce the amount of time that a patient must hold their eye steady, which can lead to lower quality of data acquired. The longer a patient must hold his eye steady, the more his eye may dry out which also reduces image quality, as well as leads to discomfort and natural eye movement.

Another approach to solving this problem could involve something similar to a motion picture projector. This solution would utilize a mechanical shutter which would shield the light from the lamp, while the slit source is moving. This then allows a second lamp to expose a slit image onto the eye for data capture while the first motor is moving the first slit source. However, accomplishing this would require a very rapid shutter system, which would need to be electronically synchronized to the analog video camera. This approach would be costly and complicated. In addition, the use of mechanical parts would lead to failures due to worn mechanical parts.

Therefore, it would be desirable to provide a solution where the amount of exam time is greatly reduced while providing for a relatively simple and inexpensive means for acquiring the necessary images.

DETAILED DESCRIPTION

Figure 1:
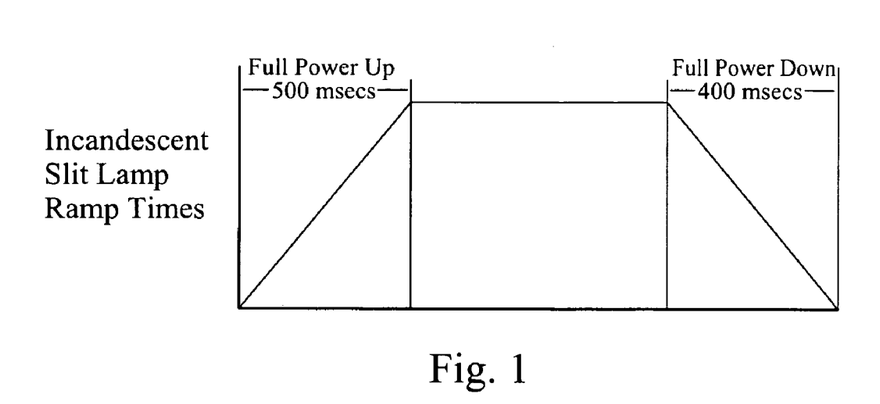
FIG. 1 is a graphical representation of the power-up and power-down ramp times of an incandescent slit lamp.
Figure 2:
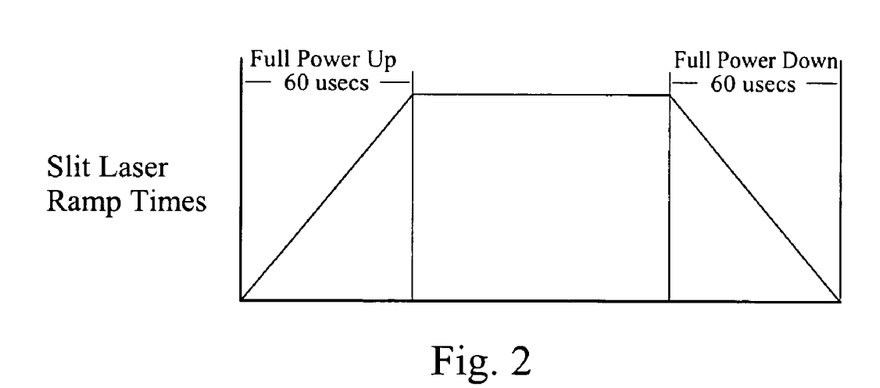
FIG. 2 is a graphical representation of a typical power-up and power-down ramp times for a laser slit lamp.

FIG. 1 is a timing diagram showing the power-up and power-down ramp times for a typical incandescent slit lamp used in a prior art slit scan image capture system. Though not on the same scale as FIG. 1, FIG. 2 shows the ramp times for a typical laser or LED light source to ramp-up to full power or ramp-down to a effectively off state. As can be seen from comparing FIG. 1 to FIG. 2, FIG. 2 requires essentially more than 4 orders of magnitude less time for the light source to power-up and power-down. As will be described in more detail below, this very fast time period for powering-up and powering-down a light source enables a much more efficient and fast slit scan image capture system, in accordance with the present invention.

Figure 3:
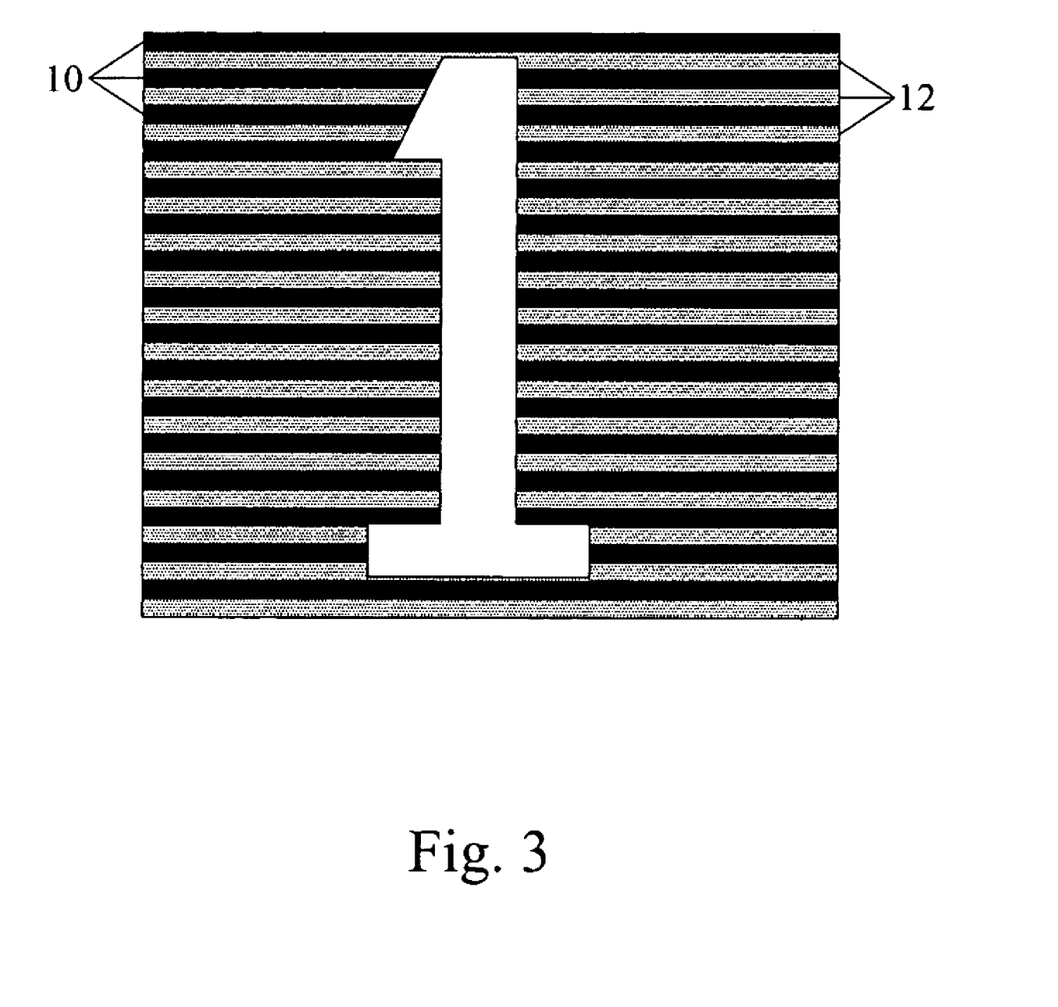
FIG. 3 is an interlaced video image of the numeral 1.

Images captured on typical prior art image capture systems, as well as preferably in the present invention, use an interlaced video image, such as shown in FIG. 3. FIG. 3 shows an image of the numeral 1 captured as interlaced video in a typical 640×480-pixel frame. This interlaced video image is well known to those skilled in the art, and has odd lines 10 shown as the black or dark lines and the even pixel lines 12 shown as the lighter shaded areas or gray lines. Such interlaced video is used in prior art systems, such as the Orbscan™ system available from Bausch & Lomb Incorporated and described in patents such as U.S. Pat. Nos. 5,512,966 and 5,512,965, both of which are incorporated herein by reference. It is noted that an interlaced video image is preferred but other video images such as progressive scan images may also be used.

Figure 4:
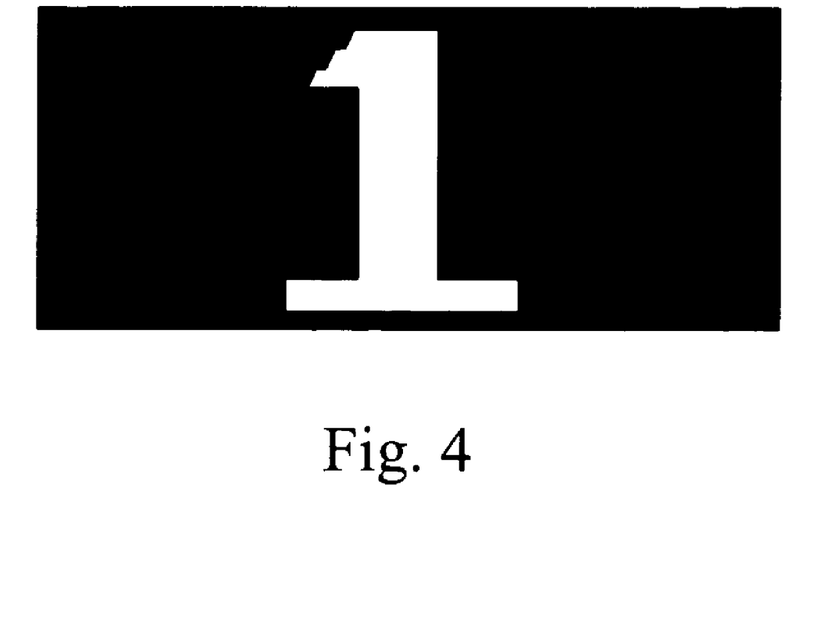
FIG. 4 is an interlaced video image of the odd fields of FIG. 3.
Figure 5:
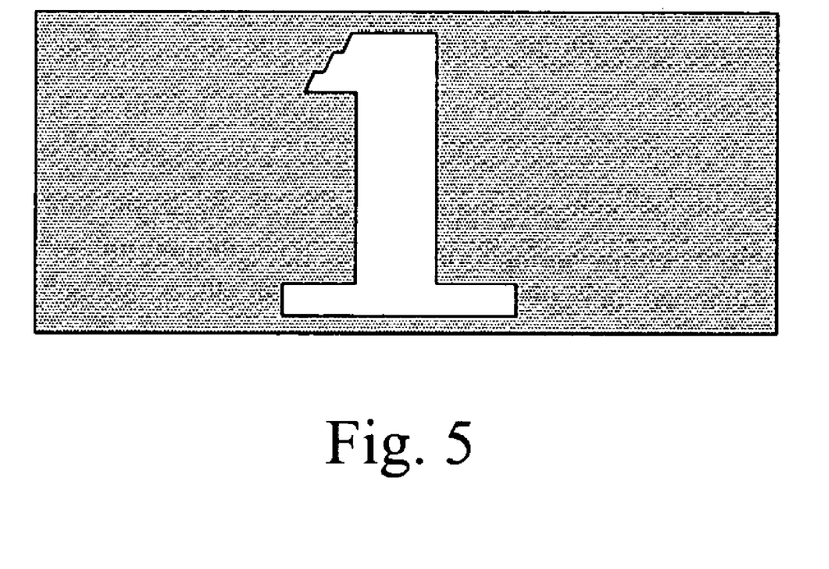
FIG. 5 is an interlaced video image of the even fields of FIG. 3.

Typically in image capture systems, the interlaced video image of FIG. 3 is segregated into odd and even fields, such that you end up with the images of FIGS. 4 and 5 where each image is 640×240 pixels and comprise only data from the odd or even fields 10 and 12. In this illustrative example, FIG. 4 contains all the odd field data 10 from the interlaced frame of FIG. 3, and FIG. 5 contains all the even field data 12 from the interlaced frame of FIG. 3. Such segregation of the odd and even fields as shown in FIG. 4 and 5 is well known to those skilled in the art.

A typical prior art slit scan image capture system uses the ability to segregate the odd and even fields to obtain or capture a slit scan image in the odd field while using the time required by the frame grabber to acquire the even field to move the slit image in order to be in position to capture another slit image during the next odd field scan by the video system.

Figure 6:
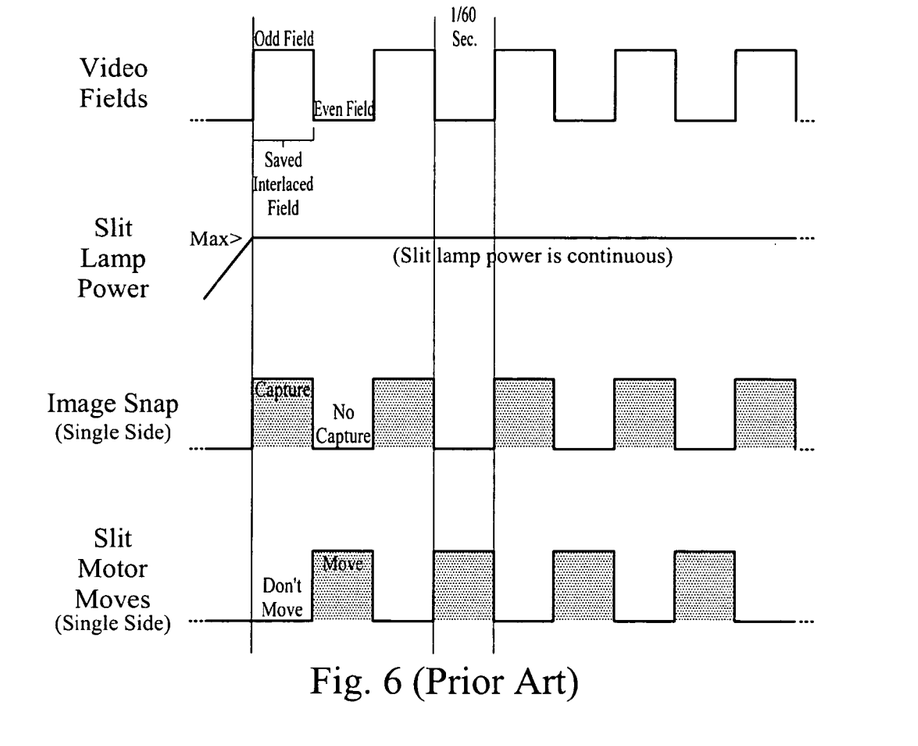
FIG. 6 is a prior art timing diagram showing the procedure for an incandescent light source slit scan image capture system.

This can be seen in the timing diagram of FIG. 6, which shows a typical prior art timing diagram. The top diagram shows a timing diagram for an interlaced video system where the time required to obtain or capture an odd or even field is shown. Typically each field requires approximately one-sixtieth of a second (1/60 sec) to be exposed. As can be seen, the slit lamp power from a typical incandescent slit lamp is ramped-up to full power and is continuous throughout the image capture time. This is because a typical incandescent slit lamp of the prior art requires at least 400 milliseconds to power-up or power-down as shown above in FIG. 1; whereas the time period for either the odd or even field capture is approximately 16.7 milliseconds, and therefore the slit lamp is required to be on continuously.

Typically when capturing an image, a slit scan image capture system scans slits across each eye from both the left and the right sides. This allows reliable data to be obtained over a large enough area of a patient's eye in order to provide a comprehensive analysis of the eye. FIG. 6 shows the prior art timing diagram for image capture and slit motor movement for moving a slit image source causing slit images to be projected across a patient's eye on only a single side. In practice, the same image capture would have to be repeated for the second side to capture enough data for one eye. As can be seen, the video camera and video system of a slit scan image capture system of the prior art, captures a video image during the odd field scan and then no image is captured during the even field scan. During this time, the slit motor moves the slit image source to a next position for capturing the next slit image of the eye. An image is captured during the odd fields while the slit motor is held stationary and the slit motor is moved while no image is being captured during the even field scan. In this way, during the motor movement a smear of light, which would be caused by motor movement, is avoided, as well as avoiding the need for any complicated and expensive mechanical shuttering mechanisms. However, as can be seen from the timing diagram of FIG. 6, by not capturing any data during the even field scans essentially half the amount of time required to capture images is wasted because of the need to move the slit image source. The more time a patient is required to hold their eye still for the exam, the more likely discomfort to the patient will be experienced, also lower quality data will be captured due to the patient's eyes drying and natural eye motion.

Figure 7:
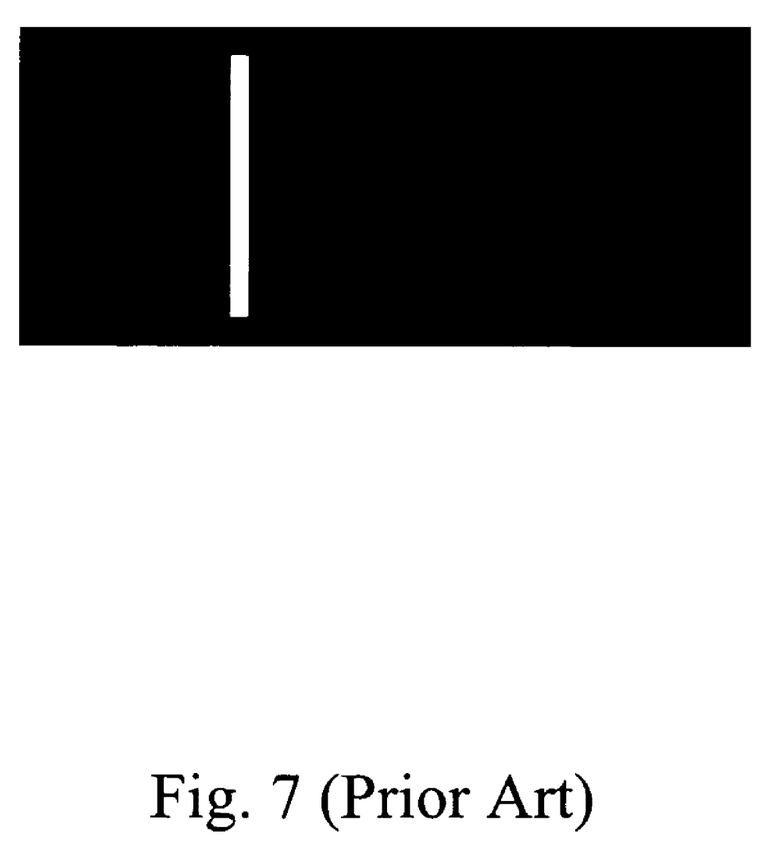
FIG. 7 is a typical slit image acquired by the prior art system described in FIG. 6.

A typical prior art system then segregates the odd field data into a frame, such as shown in FIG. 7 for each slit image captured for a patient's eye.

The present invention solves the timing problem of the prior art and makes effective and efficient use of the interlaced video scanning time through use of rapid switching light sources, such as lasers or high-luminescence light emitting diodes (HL-LEDs), such as Schäfter & Kirchhoff Type 13L . . . +90 Laser and HL-LED part number LXHL-NW98 from www.lumileds.com. Of course, other light sources could be used if they are capable to being switched fast enough.

Figure 8:
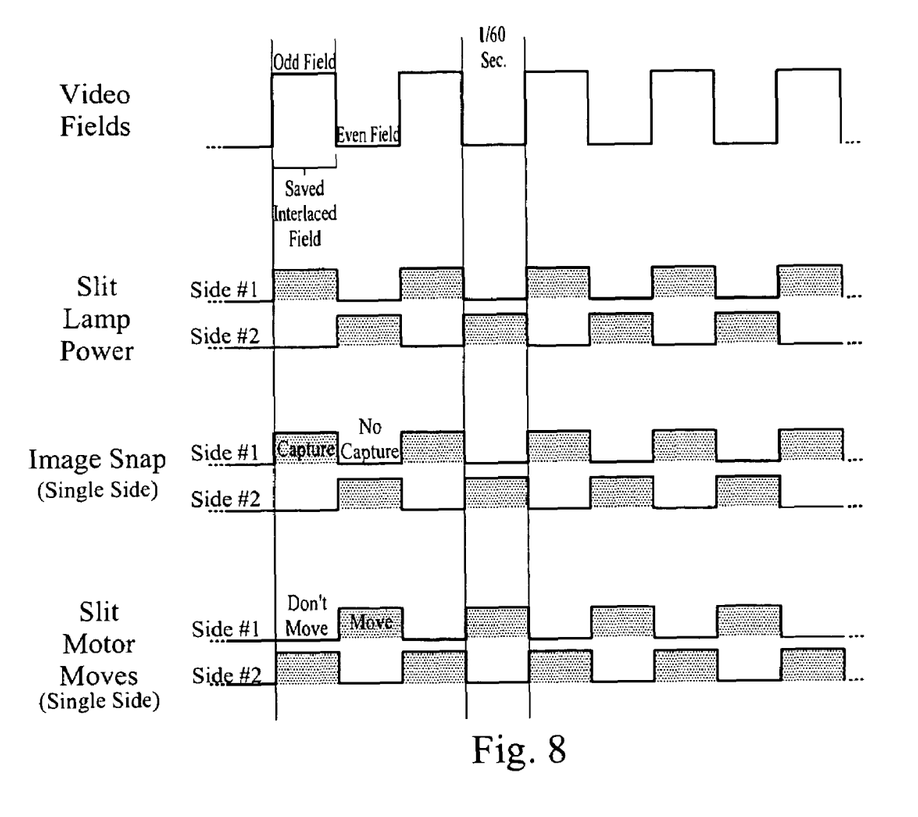
FIG. 8 is a timing diagram of a system using a rapid switching laser or HL-LED light source, in accordance with the present invention.

FIG. 8 shows a slit laser-timing diagram, in accordance with the present invention. As can be seen, the same odd and even field frame scanning time is shown as that shown in FIG. 6. However, two slit laser power timing diagrams are shown, such that the slit laser ramp times are essentially those shown in FIG. 2, and require less than 100 microseconds to either ramp-up to essentially full power or ramp-down to an essentially off state. As can be seen in FIG. 8, rapid switching light sources power up to an approximately full power state and powers down to an effectively off state in an amount of time less than the amount of time required by the motor to move a slit image source from one position to the next. Typically, a single motor requires approximately 16.7 milliseconds to move from one position to a next, such that the slit image source is stabilized from one position to the next. This rapid switching minimizes the amount of time required to capture a plurality of slit images across major portions of the patient's eye. This is so because images can now be captured in both the odd and the even fields, as shown in the timing diagram of FIG. 8. As an image is being captured with side one's slit laser at full power, side two's slit laser or HL-LED light source is off, the slit motor of side two moves it's slit image source into position so that side two's slit laser or HL-LED light source is powered up and it's image is captured in the first even field while side one motor moves the slit mask or mirror for side one. Such a timing scheme is simply impossible using prior art incandescent light sources.

A typical eye exam obtains 40 slit images. The time required to obtain these images for the present invention is approximately 0.7 seconds (20 frames@1/30 sec). This is significantly lower than the prior acquisition time of about 1.7 seconds.

Figure 9:
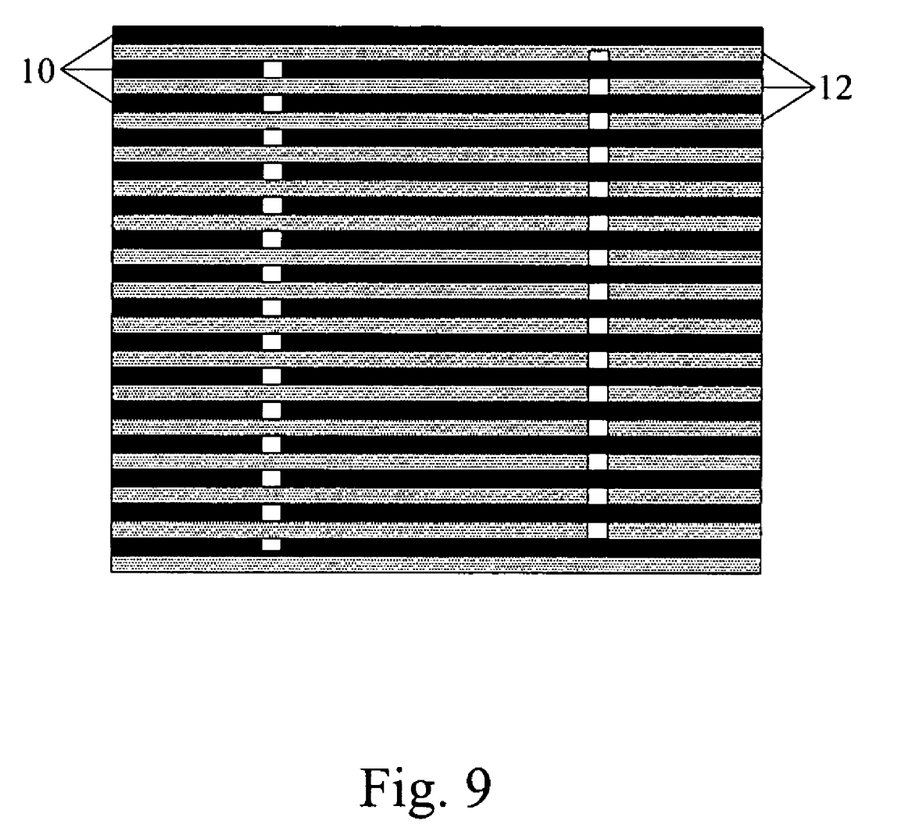
FIG. 9 is a resultant video image of slits captured with a system in accordance with the present invention.

FIG. 9 shows a resultant interlaced video frame of slit images captured, in accordance with the present invention. The odd lines 10 contain slit images from side number one and even field lines 12 contain images from slit image source number two. These interlaced video images are then segregated by known means into odd and even segregated frames, such as described above with relation to FIGS. 4 and 5.

Figure 10:
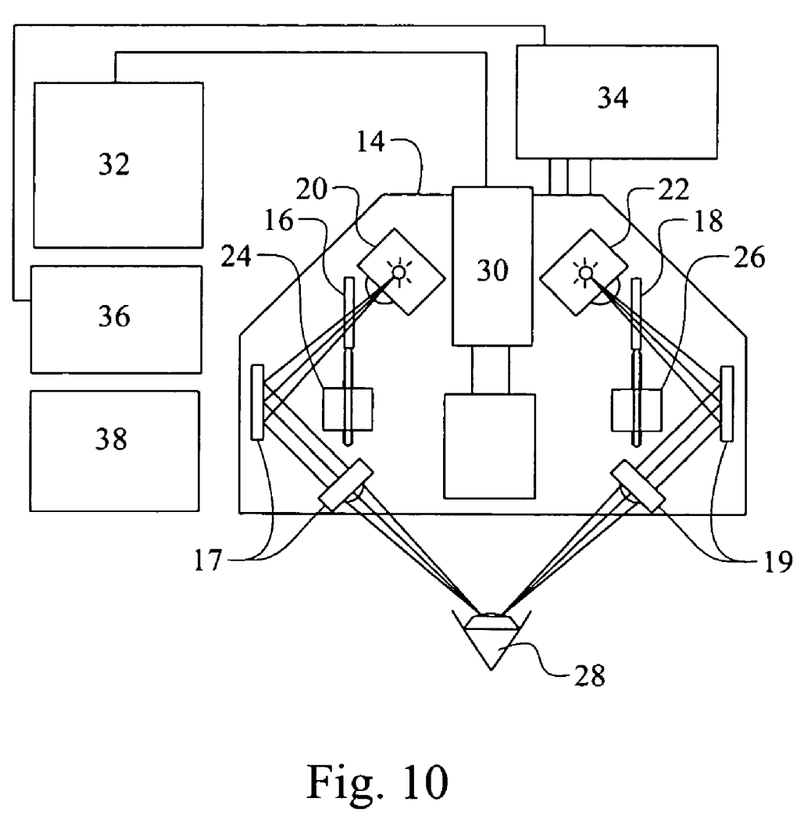
FIG. 10 is a block diagram of a slit scan image capture system using a slit mask moving across a focused point light source, in accordance with the present invention.

FIG. 10 shows a slit scan image capture system 14 for obtaining slit images of a patient's eyes using a slit mask moving across a focused point light source, in accordance with the present invention. At least two slit masks 16 and 18 are associated with at least two rapid switching focused point light sources 20 and 22, reflected off stationary mirrors and lenses 17 and 19, such that at least two slits may be illuminated on the patient's eye. At least two motors 24 and 26 are connected to the slit masks 16 and 18 respectively for incrementally moving the illuminated slits across the eye 28 to a plurality of positions. A combination of slit mask 16, light source 20, stationary mirror and lens 17, and motor 24 form side number one of the timing diagram of FIG. 8, and elements 18, 22, 19, and 26 combine to form side number two.

Figure 11:
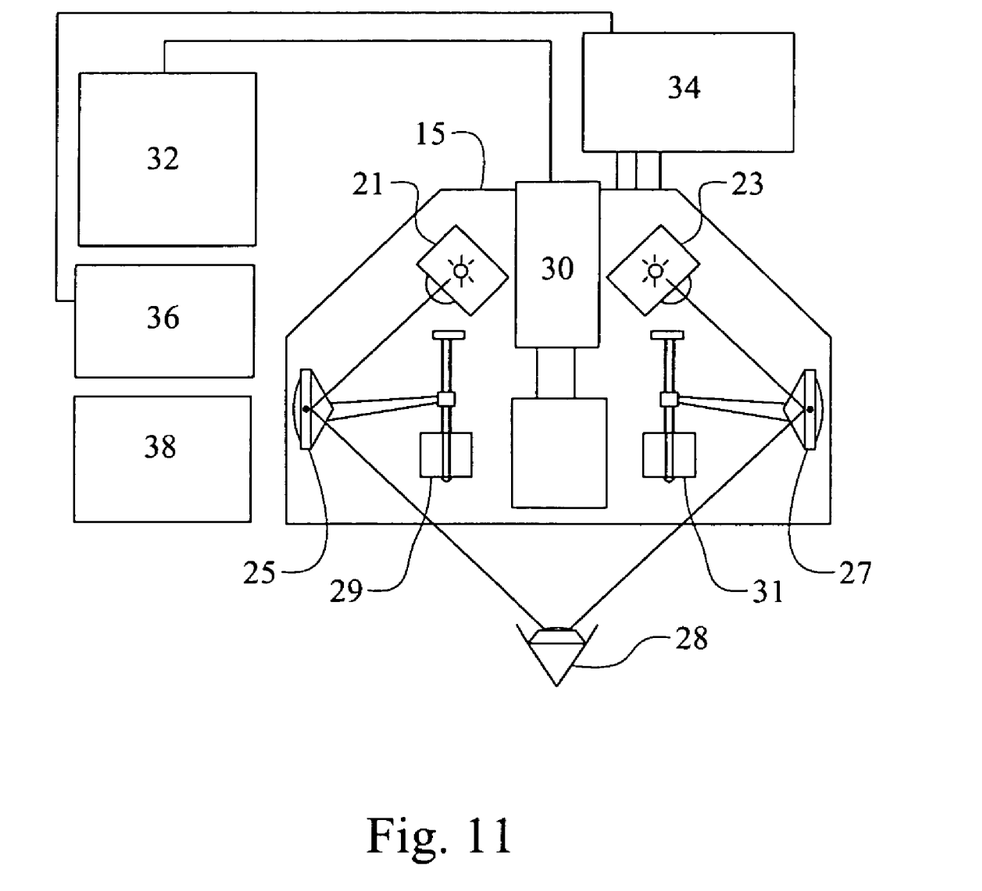
FIG. 11 is a block diagram of an alternative slit scan image capture system using a stationary slit source and a movable mirror for scanning the eye, in accordance with the present invention.

FIG. 11 shows an alternative slit scan image capture system 15 for obtaining slit images of a patient's eyes using a stationary slit source and a movable mirror for scanning the eye, in accordance with the present invention. At least two movable mirrors 25 and 27 are associated with at least two rapid switching stationary slit light sources 21 and 23, such that at least two slits may be illuminated on the patient's eye. At least two motors 29 and 31 are connected to the movable mirrors 25 and 27 respectively for incrementally moving the illuminated slits across the eye 28 to a plurality of positions. A combination of light source 21, movable mirror 25, and motor 29 form side number one of the timing diagram of FIG. 8, and elements 23, 27, and 31 combine to form side number two.

Referring to both FIGS. 10 and 11, a video camera 30 for capturing images of the illuminated slits on the eye 28 is connected to a frame grabber 32 for storing the captured images. The rapid switching light sources 20 and 22 power-up to an approximately full power state and power-down to an effectively off state in an amount of time less than the amount of time required by the motors 24 and 26 or motors 29 and 31 to move slit masks 16 or 18, or movable mirrors 25 or 27, from one position to a next position. This allows the amount of time required to capture a plurality of slit images across major portions of the patient's eye to be minimized.

The video camera is preferably of the type, such a Teli NTSC interlaced monochrome camera and the frame grabber is preferably an interlaced frame grabber, such as a PC-Vision and available Coreco. The slit masks 16 and 18, the movable mirrors 25 and 27, the rapid switching focused point light sources 20 and 22, the rapid switching stationary slit light sources 21 and 23, and the motors 24 and 26 and 39 and 31 are all preferably part of a controller 34 for controlling the switching of the light sources and the movement of the slit masks or movable mirrors. As the first light source 20 or 21 is powered-up so that a slit image is illuminated on the eye 28 via the first slit mask 16 or movable mirror 25, the second light source 22 or 23 is powered-down and a second slit mask 18 or movable mirror 27 is caused to move to a next position, such that a time to power-up or power-down a light source 20 or 21 or 22 or 23 is less than the time required to move a slit mask 16 or 18 or movable mirror 25 or 27 to a next position relative to the patient's eye 28. This allows for each field of an interlaced frame to contain data from both the first and second slit mask images illuminated on the patient's eyes. Controller 34 is preferably part of a system console 36 which also includes CPU 38 for analyzing the captured slit images and providing data to a practitioner, such as topography, corneal thickness, and other diagnostic information on the eye 28 that has been scanned.

I claim:

1. A slit scan image capture system for obtaining slit images of a patient's eyes comprising:
    at least two slit image sources;
    at least two rapid switching light sources, wherein one of the light sources is associated with one slit image, such that at least two slits may be illuminated on the patient's eyes;
    at least two motors, each connected to the slit image sources for incrementally moving the illuminated slits across the eye to a plurality of positions;
    a video camera for capturing images of the illuminated slits on the eye;
    a frame grabber connected to the video camera for storing the captures images; and
    wherein the rapid switching light sources power-up to approximately a full-power state and power-down to an effectively off state in an amount of time less than the amount of time required by the motor to move a slit image from one position to a next position, thereby minimizing an amount of time required to capture a plurality of slit images across major portions of the patient's eyes.

2. The invention of claim 1, wherein the rapid switching light sources are lasers or light emitting diodes.

3. The invention of claim 1, wherein each of the slit image sources includes a slit mask, the motor moves the slit masks from one position to a next position in about 1/60 of a second.

4. The invention of claim 1, wherein the frame grabber is an interlaced frame grabber.

5. The invention of claim 1, wherein the frame grabber is a progressive scan frame grabber.

6. The invention of claim 1, wherein the light sources power-up or power-down in less than 100 microseconds.

7. A slit scan image capture system for obtaining slit images of a patient's eyes comprising:
    at least first and second slit image sources;
    at least first and second rapid switching light sources, wherein the first light source is associated with the first slit image source and the second light source is associated with the second slit image source such that at least two slit images may be illuminated on the patient's eyes;
    a video camera for capturing images of the illuminated slits on the eye;
    an interlaced frame grabber connected to the camera for storing the captured images; and
    a controller for controlling the switching of the light sources and the movement of the slit image sources wherein as the first light source is powered-up so that a slit image is illuminated on the eye via the first slit image source, the second light source is powered-down and the second slit image source is caused to move to a next position, such that a time to power-up or power-down a light source is less than the time required to move a slit image source to a next position relative to the patient's eyes, thereby allowing each field of an interlaced frame to contain data from both the first and second slit image source's images illuminated on the patient's eyes.

8. The invention of claim 7, wherein the rapid switching light sources are lasers or light emitting diodes.

9. The invention of claim 7, wherein the controller includes motors connected to slit masks or movable mirrors for incrementally moving the illuminated slits across the eyes to a plurality of positions.

10. The invention of claim 9, wherein the motors move the slit source from one position to a next position in about 1/60 of a second.

11. The invention of claim 7, wherein the light sources power-up or power-down in less than 100 microseconds.

12. A method of operating a slit scan imaging system for obtaining slit images of a patient's eyes comprising the steps of:
    providing at least first and second slit image sources;
    associating first and second rapid switching light sources with each
    slit image source for illuminating slit images on the patients eyes;
    providing a video camera for capturing Images of the illuminated slits on the eyes;
    connecting an interlaced frame grabber to the video camera for storing the captured images; and
    controlling the switching of light sources and the movement of the slit image sources wherein as the first light source is powered-up so that a slit image is illuminated on the eye via the first slit image source, the second light source is powered-down and the second slit image source is caused to move to a next position such that a time to power-up or power-down a light source is less than the time required to move a slit image source to a next position relative to the patients eye, thereby allowing each field of an interlaced frame to contain data from both the first and second slit image source's images illuminated on the patient's eye.

13. The method of claim 12, wherein the light sources are lasers or light emitting diodes.

14. The method of claim 12, wherein the time to power-up or power-down a light source is less than 100 microseconds.

15. The method of claim 12, wherein the controlling step includes connecting motors to each of a slit mask or a movable mirror for moving the illuminated slits across the patient's eyes.

* * * * *